United States Patent
Coronel

(10) Patent No.: US 7,624,480 B2
(45) Date of Patent: Dec. 1, 2009

(54) HOOK AND LOOP FASTENING STRAP AND ASSEMBLY

(75) Inventor: Wolfgang Coronel, Macon, GA (US)

(73) Assignee: YKK Corporation of America, Marietta, GA (US)

( * ) Notice: Subject to any disclaimer, the term of this patent is extended or adjusted under 35 U.S.C. 154(b) by 78 days.

(21) Appl. No.: 11/835,014

(22) Filed: Aug. 7, 2007

(65) Prior Publication Data

US 2009/0038123 A1 Feb. 12, 2009

(51) Int. Cl.
*A44B 18/00* (2006.01)
(52) U.S. Cl. .................. 24/306; 24/16 R; 128/DIG. 15
(58) Field of Classification Search ............ 24/306, 24/442, DIG. 29, 16 R; 128/DIG. 15, DIG. 26; 428/100; 248/205.2; 604/174, 179, 180
See application file for complete search history.

(56) References Cited

U.S. PATENT DOCUMENTS

| | | | | |
|---|---|---|---|---|
| 2,361,506 A | * | 10/1944 | Smith et al. | 602/58 |
| 2,961,785 A | * | 11/1960 | Toepfer | 40/669 |
| 4,477,950 A | * | 10/1984 | Cisek et al. | 24/30.5 P |
| 4,617,017 A | | 10/1986 | Hubbard et al. | |
| 5,300,037 A | | 4/1994 | Delk et al. | |
| 2003/0110596 A1 | | 6/2003 | Graham et al. | |

OTHER PUBLICATIONS

Dale Medical—Foley Catheter Holder; Product Info; available at http://www.dalemed.com/prod/foleycatheter.html; pp. 1-2, retrieved Sep. 19, 2007.
Velcro USA Inc. Industrial Products: Velcro® Brand One-Wrap® Fasteners; available at http://www.welcro.com/industrial/one.html, pp. 1, retrieved Sep. 19, 2007.
Cath-Secure Full Face Shields Medical Tube Holder Medical Supply Company Surgical; Products; available at http://www.mcjohnson.com/products.php, pp. 1, retrieved Sep. 19, 2007.
United Kingdom Search Report of UK Patent Application No. GB0811753.3, dated Oct. 13, 2008.

\* cited by examiner

*Primary Examiner*—James R Brittain
(74) *Attorney, Agent, or Firm*—Alston & Bird LLP

(57) ABSTRACT

Various embodiments of the invention provide an elongated hook and loop fastening strap with a slit defined therein for securing one or more objects together. The fastening strap includes an engaging portion, which is disposed generally above the slit, and an anchor portion, which is disposed generally below the slit. The engaging portion is peeled away from a base to which the anchor portion is attached and is wrapped around the objects to be secured. The engaging portion is then threaded through the slit and engaged onto the base. The engaging shear force between the anchor portion of the strap and the base is sufficient to hold the strap to the base when the engaging portion is peeled away from the base, alleviating the need for external bonding methods for securing the strap to the base and allowing a user to secure the strap using one hand.

13 Claims, 8 Drawing Sheets

HOOK AND LOOP FASTENING STRAP AND ASSEMBLY

BACKGROUND OF THE INVENTION

Hook and loop fastening straps may be used in various applications to secure objects adjacent a base that has hooks or loop material on its upper surface and adhesive on its lower surface. For example, the lower surface of the base may be adhered to the skin of a patient and the strap secured to the base may be used to immobilize a catheter that has been inserted into the patient's body adjacent the base. In another example, the base may be secured to a wall, an appliance, or a cabinet and the strap may be used to hold cables or wires against the base.

Various conventional hook and loop fastening straps define holes through which one end of the strap passes to secure objects adjacent to the strap, such as shown in FIG. 1. However, when an engaging end of such a strap is threaded through a hole in the strap, the hooks (or loop material) on the lower surface of the strap tend to catch on the loop material (or hooks) of the base adjacent the hole, which often results in the user needing both hands to guide the strap through the opening while avoiding unintentional engagement with the base.

In addition, straps are typically permanently or semi-permanently secured to the bases using bonding methods other than the engagement (or shear) force of the hooks and loop material between the strap and the base to prevent complete removal of the strap from the base when the strap is being engaged around the object to be secured. For example, the bonding methods may include sewing, ultrasonic or RF welding, heat lamination, or using pressure sensitive adhesives. An example of this type of assembly is shown in U.S. Pat. No. 4,617,017. The need to use an additional bonding method to secure the strap to the base can be cumbersome and time consuming and it prevents the user from being able to reposition the strap on the base. Furthermore, at least some of the above noted bonding methods, such as using pressure sensitive adhesives, may break down and fail over time.

Accordingly, a need in the art exists for an improved hook and loop fastening strap and assembly.

BRIEF SUMMARY OF THE INVENTION

Various embodiments of the invention provide a fastening strap for securing one or more objects together. The fastening strap includes: (1) an upper surface, (2) a lower surface opposite the upper surface that includes hooks or loop material for engaging loop material or hooks, respectively, (3) an anchor end, (4) an engaging end, and (5) an elongated body extending between the anchor end and the engaging end. The elongated body defines a slit, and the slit has two ends and an intermediate portion between the ends. The ends are disposed toward the anchor end relative to the intermediate portion along a longitudinal axis of the elongated body. In addition, the elongated body includes a tongue that is disposed between the ends and the intermediate portion of the slit and two leg portions that are disposed laterally adjacent each side of the slit and the tongue relative to the longitudinal axis. The leg portions have a combined width that is less than a width of a foot of the tongue, and the foot of the tongue is disposed along a generally transverse axis extending through the ends of the slit. In addition, the engaging end has a width that is less than the width between of the foot of the tongue to allow the engaging end to pass through an opening that is defined by the foot of the tongue and the leg portions when the engaging end of the strap is pulled toward the anchor end.

In one embodiment, the intermediate portion of the slit is generally arcuate shaped. In another embodiment, the intermediate portion of the slit and the foot of the tongue form a generally triangular shaped opening when said engaging end of the strap is pulled toward the anchor end. In yet another embodiment, the intermediate portion of the slit and the foot of the tongue form a generally rectangular shaped opening when the engaging end of the strap is pulled toward the anchor end.

According to various embodiments, a hook and loop fastener assembly is provided for securing one or more objects adjacent a base. The assembly includes a base and a fastening strap, such as the straps described above. The base includes an upper surface, and at least a portion of the upper surface defines a field of hooks or loop material for engaging corresponding loop material or a field of hooks, respectively, on the lower surface of the fastening strap. To secure said one or more objects adjacent the strap and base, one or more objects are disposed adjacent the foot of the tongue of the strap, and the engaging end of the strap is pulled upwardly from the base and toward the anchor end and is threaded between the one or more objects and the tongue through the opening defined by the foot of the tongue and the leg portions. At least a portion of the lower surface of the elongated body that has passed through the opening is then engaged onto the base. In one embodiment, the base includes an adhesive material on the lower surface.

The additional bonding methods used in the prior art straps are not necessary for various embodiments of the present invention because the shear force between the strap and the base at the foot of the tongue is substantially greater than the peeling force required to peel the engaging end and the leg portions upwardly from the base. In addition, according to various embodiment, the tongue allows the lower surface of the engaging end of the strap to pass easily through the opening in the strap, which may prevent the need for a two handed assembly of the strap relative to the base.

BRIEF DESCRIPTION OF THE DRAWINGS

Figure 1:
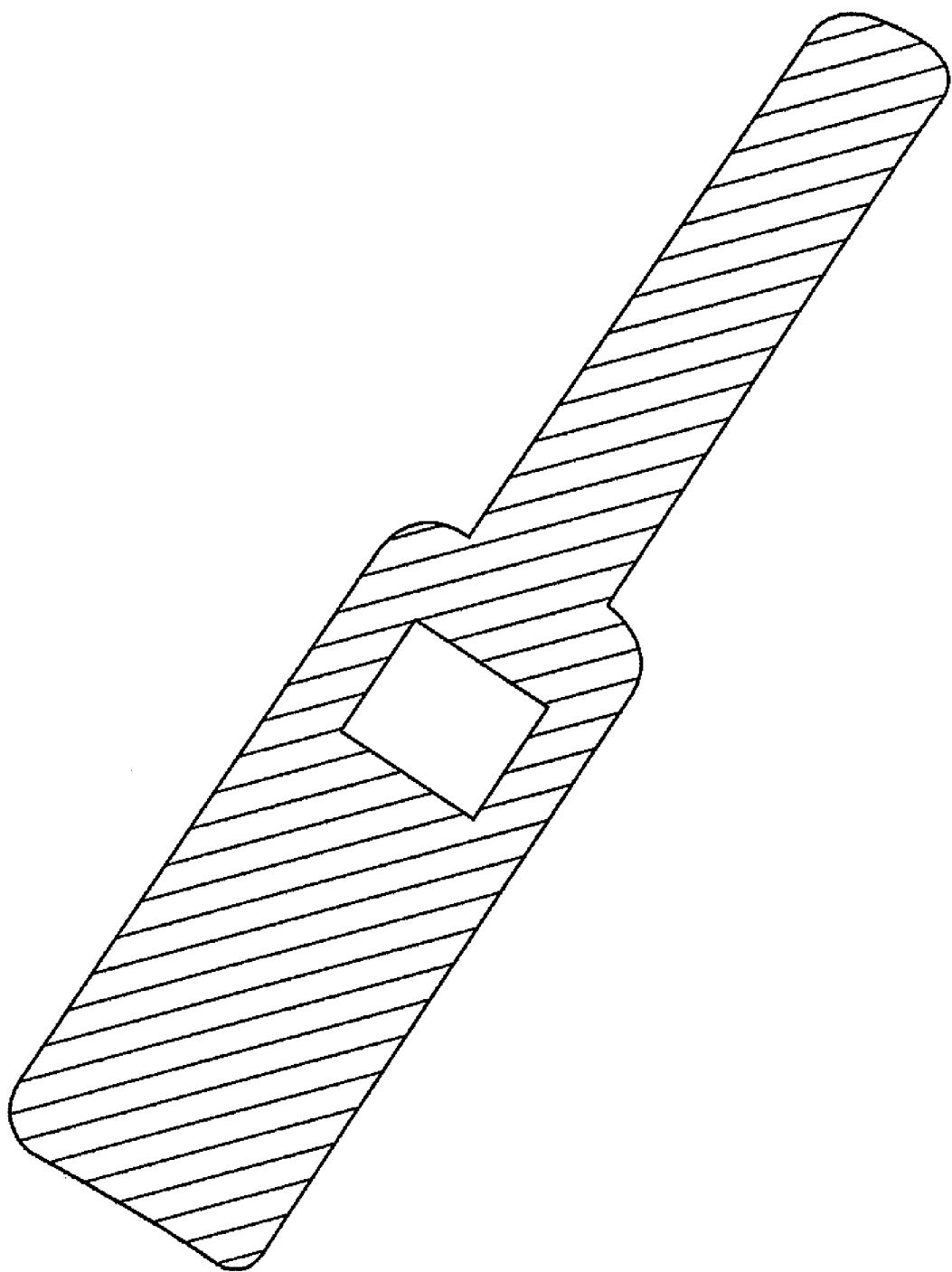

Having thus described various embodiments of the invention in general terms, reference will now be made to the accompanying drawings, which are not necessarily drawn to scale, and wherein:

FIG. 1 illustrates an upper perspective view of a prior art fastening strap assembly.

Figure 2:
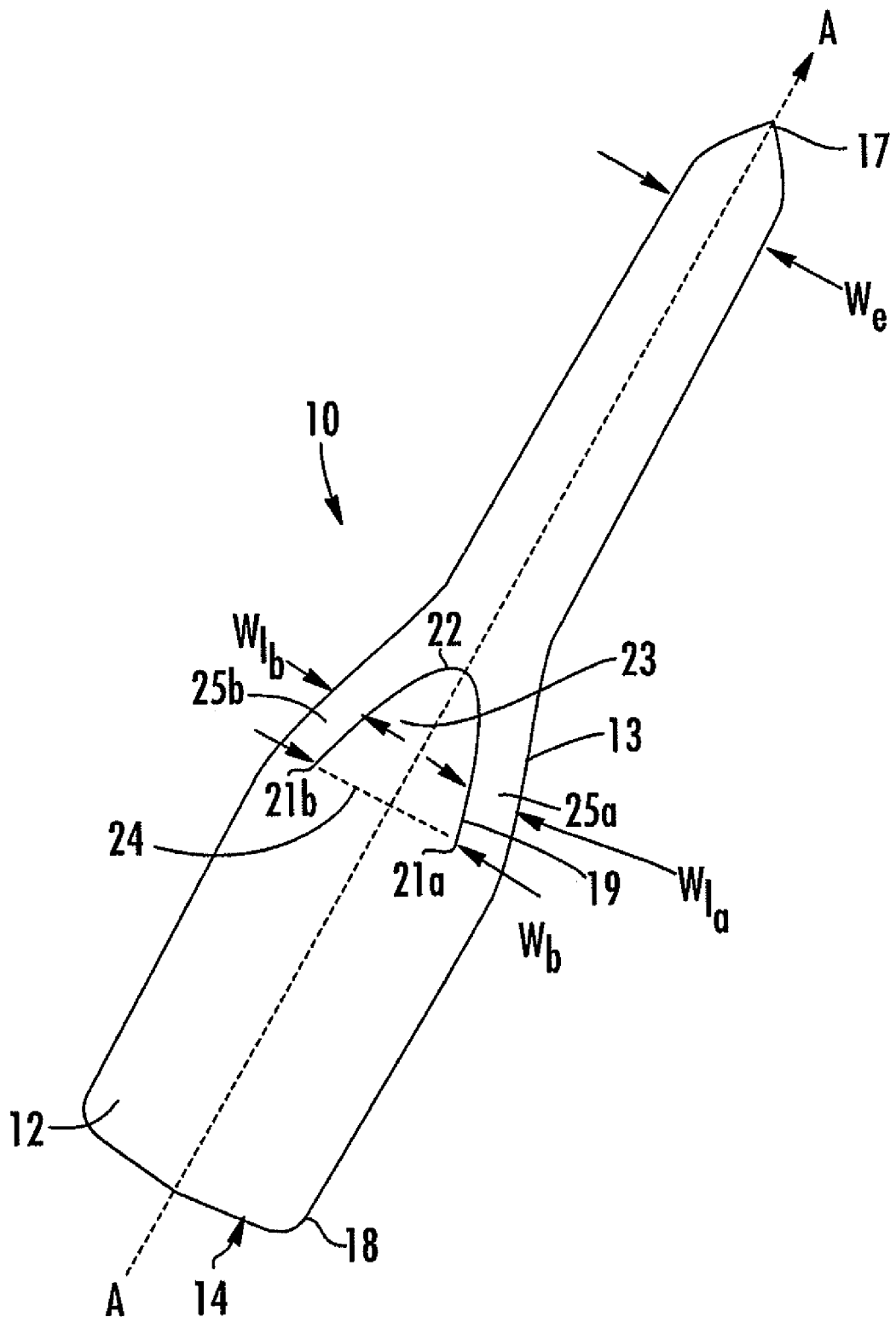

FIG. 2 illustrates an upper perspective view of a fastening strap according various embodiments of the present invention.

Figure 3:
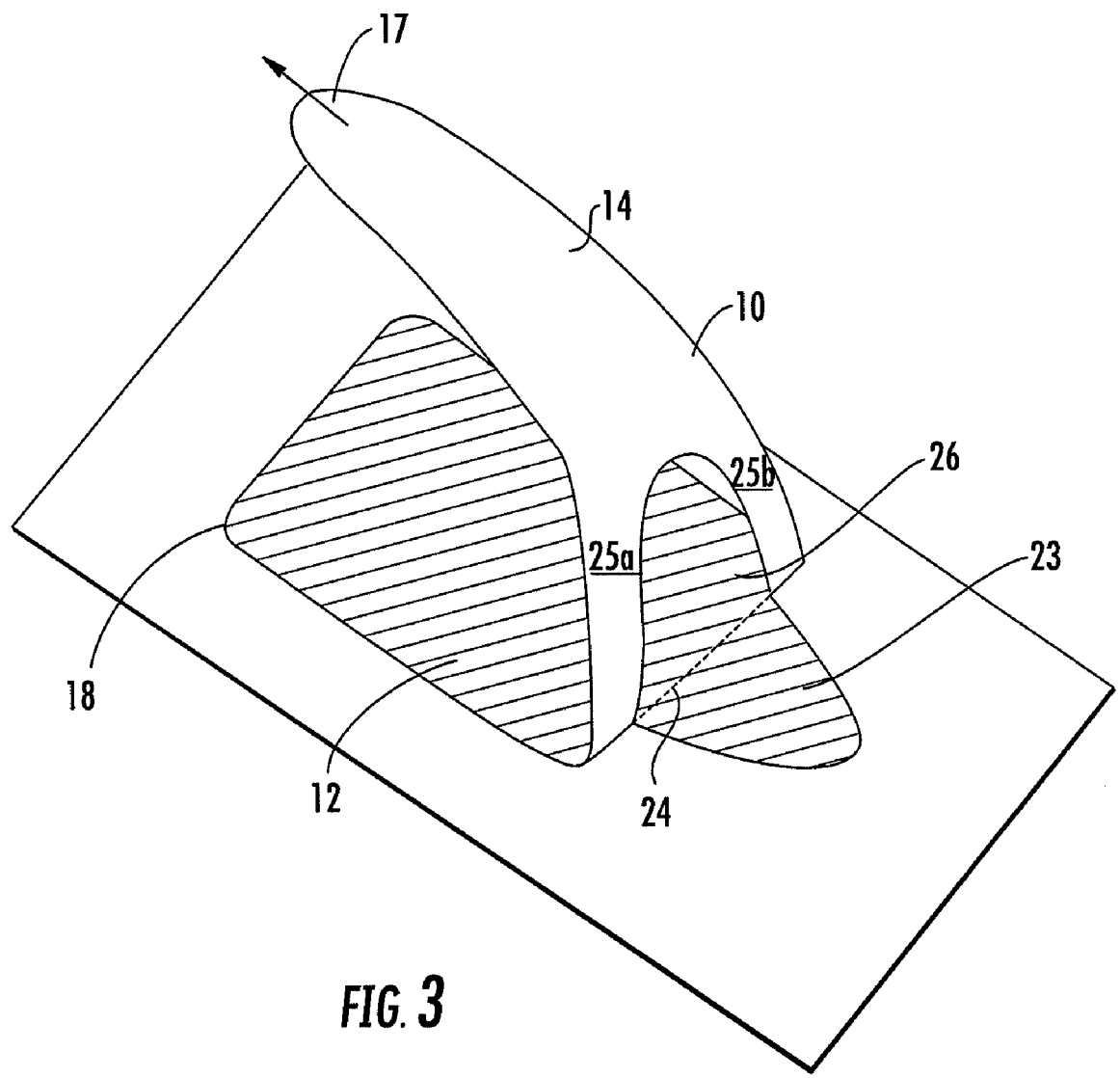

FIG. 3 illustrates an upper perspective view of the fastening strap of FIG. 2 being peeled upwardly and rearwardly according to one embodiment of the invention.

Figure 4:
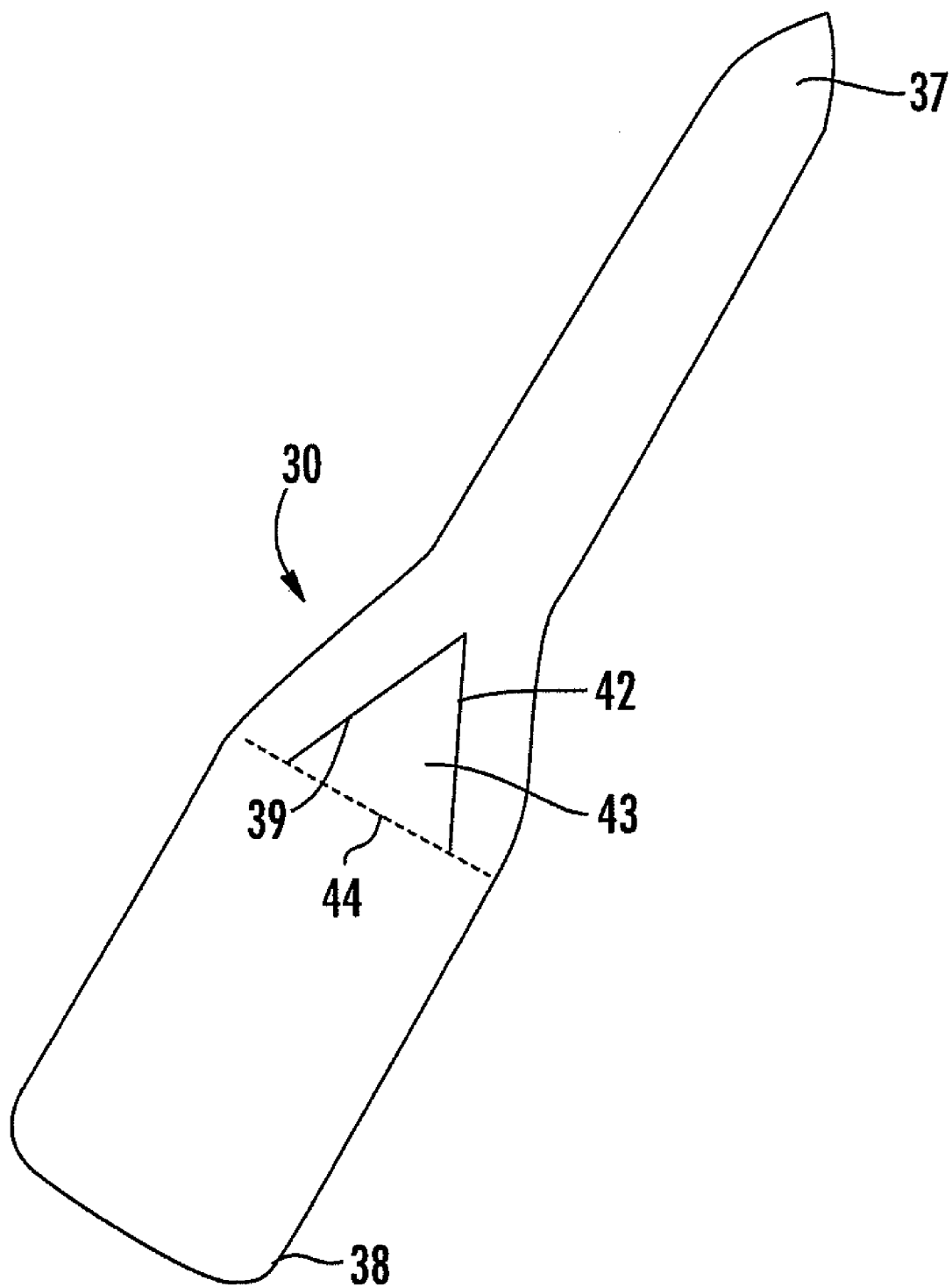

FIG. 4 illustrates an upper perspective view of a fastening strap according to another embodiment of the invention.

Figure 5:
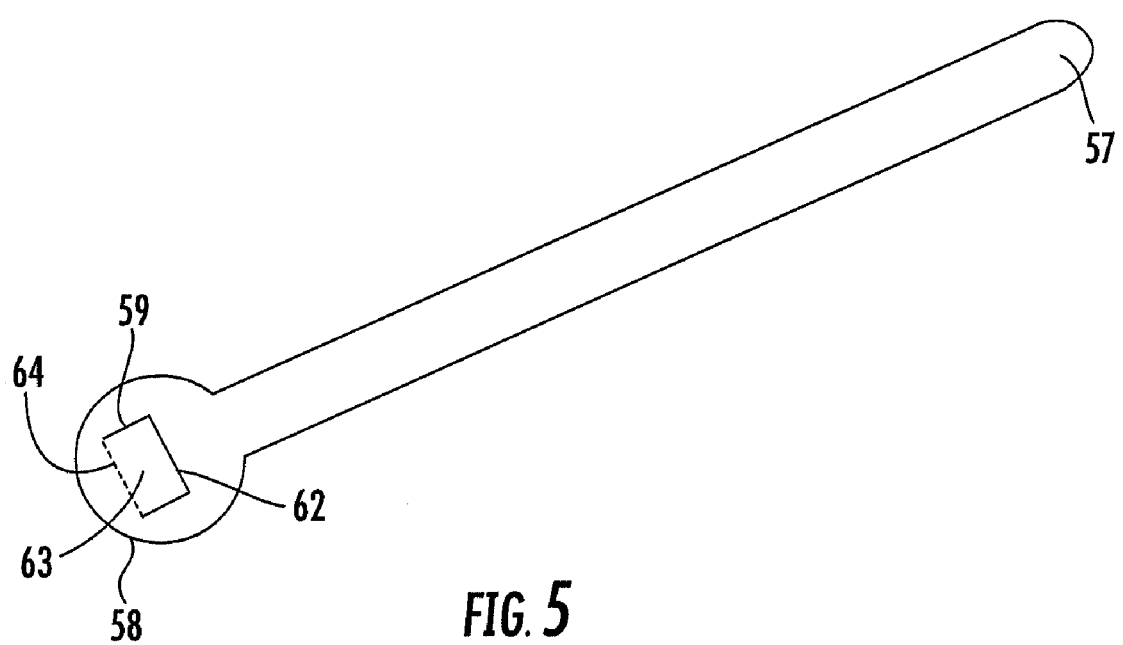

FIG. 5 illustrates an upper perspective view of a fastening strap according to yet another embodiment of the invention.

Figure 6:
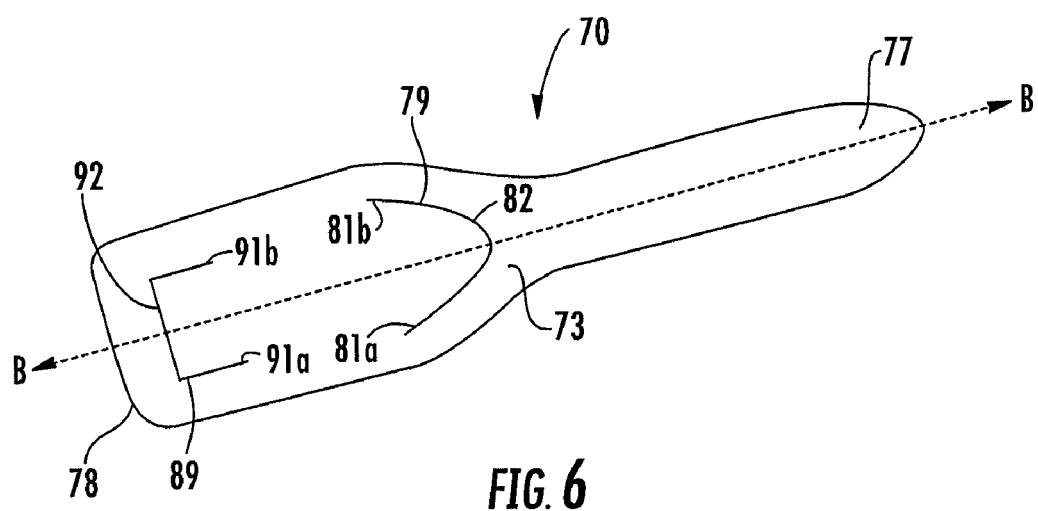

FIG. 6 illustrates an upper perspective view of a fastening strap according to yet another embodiment of the invention.

Figure 7A:
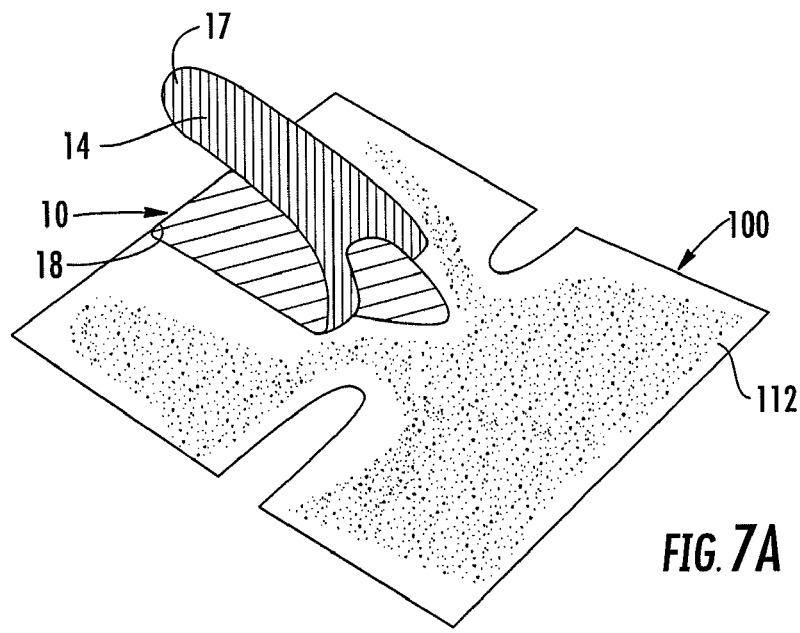
Figure 7B:
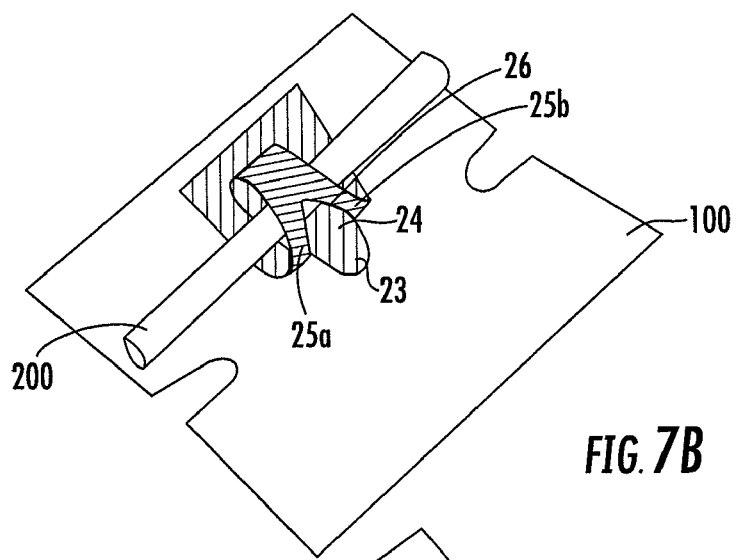
Figure 7C:
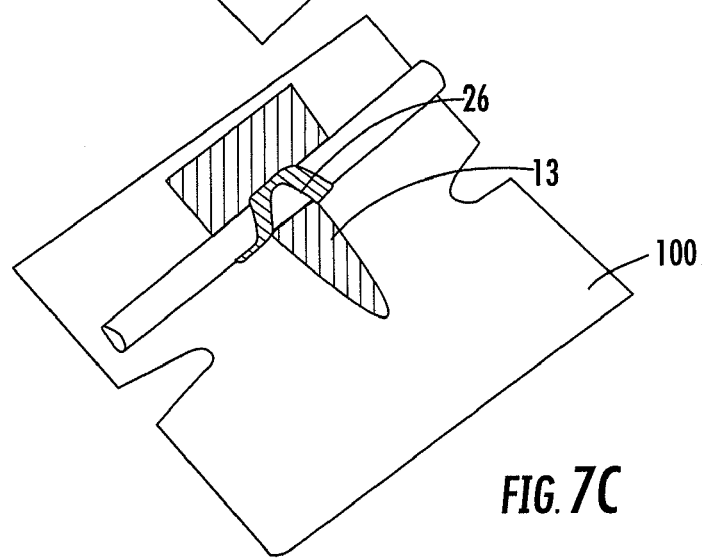

FIGS. 7A-7C illustrate the steps of engaging the strap shown in FIG. 2 to secure a catheter to a base according to various embodiments of the invention.

Figure 8A:
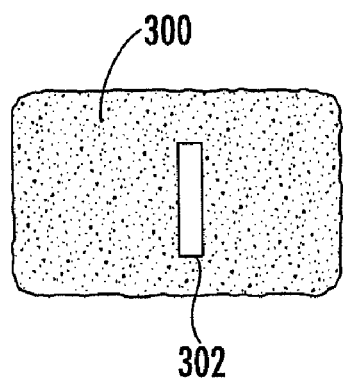

FIG. 8A illustrates an upper plan view of a base according to an alternative embodiment of the invention.

Figure 8B:
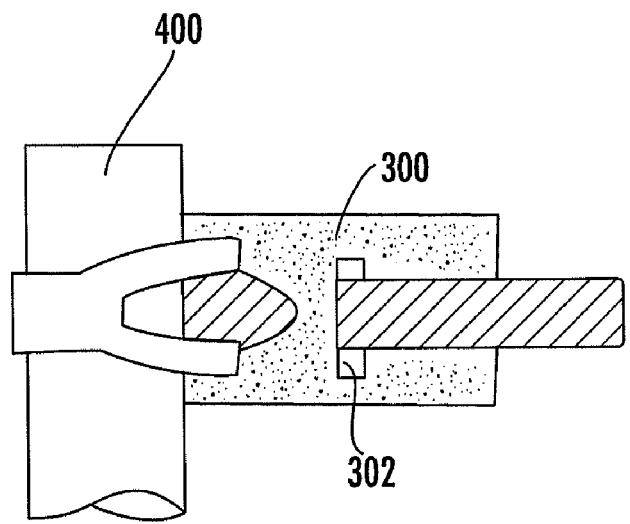

FIG. 8B illustrates an upper plan view of the base shown in FIG. 8A and a fastening strap secured to the base according to one embodiment of the invention.

DETAILED DESCRIPTION OF VARIOUS EMBODIMENTS OF THE INVENTION

Various embodiments of the invention are described more fully hereinafter with reference to the accompanying drawings, in which some, but not all embodiments of the invention are shown in the figures. Indeed, these inventions may be embodied in many different forms and should not be construed as limited to the embodiments set forth herein; rather, these embodiments are provided so that this disclosure will satisfy applicable legal requirements.

Brief Summary

Various embodiments of the invention provide an elongated hook and loop fastening strap with a slit defined therein for securing one or more objects together. The fastening strap is wrapped around the objects to be secured, and one end of the strap is threaded through the slit and engaged onto corresponding hooks or loop material. According to various embodiments, the strap provides longer lasting holding ability than straps that utilize adhesive to secure the objects together. In addition, in embodiments in which the strap is used with a base having corresponding hooks or loop material thereon, the engaging shear force between the strap and base are sufficient to hold the strap to the base, which alleviates the need for utilizing external bonding methods for securing the strap to the base and allows a user to secure the strap around the objects using one hand. Furthermore, according to various embodiments, cutting the slit in the strap may reduce the time and costs of manufacturing the strap as compared to straps that define a hole therein.

Fastening Strap

FIGS. 2 and 3 illustrate an elongated fastening strap according to one embodiment of the invention. The strap 10 includes an upper surface 12, a lower surface 14 opposite the upper surface 12 that includes a field of hooks (not shown) for engaging loop material, an anchor end 18, an engaging end 17, and an elongated body 13 extending between the anchor end 18 and the engaging end 17. The elongated body 13 defines a slit 19, and the slit 19 has two ends 21a, 21b and an intermediate portion 22 between the ends 21a, 21b. The ends 21a, 21b are disposed toward the anchor end 18 relative to the intermediate portion 22 along a longitudinal axis A of the elongated body. In addition, the elongated body includes a tongue 23 that is disposed between the ends 21a, 21b and the intermediate portion 22 of the slit 19 and two leg portions 25a, 25b that are disposed laterally adjacent each side of the slit 19 and the tongue 23 relative to the longitudinal axis A. The leg portions 25a, 25b have a combined width $(w_{1a}+w_{1b})$ that is less than a width $w_b$ of a foot 24 of the tongue 23 that lies along a generally transverse axis extending through the ends 21a, 21b of the slit 19. The width $w_e$ of the elongated body 13 adjacent the engaging end 17 is also less than the width $w_b$ of the foot 24 to allow the engaging end 17 to pass through an opening 26 (shown in FIG. 4) that is defined by the tongue 23 and the leg portions 25a, 25b when the engaging end 17 of the strap 10 is pulled toward the anchor end 18. In the embodiment shown in FIG. 3, the generally transverse axis along which the foot 24 of the tongue 23 lies is substantially perpendicular to the longitudinal axis A.

FIG. 3 illustrates the engaging end 17 being peeled upwardly from a base having loop material to which the strap is attached and rearwardly toward the anchor end 18 using a peel force (e.g., about 1 lbs./in.). When the strap 10 is peeled with the peel force, the portion of the strap between the engaging end and the slit 19 and the leg portions 25a, 25b are urged upwardly and rearwardly away from the base because the engaging shear force of the hooks and loop material of the leg portions 25a, 25b and the base, respectively, is less than the peel force being applied to the strap 10. However, the engaging shear force at the foot 24 of the tongue 23 across the width of the strap 10 (e.g., about 24 lbs./in.) is greater than the peel force, which prevents removal from the base of a portion of the strap 10 that includes the tongue 23 and the portion of the strap 10 between the foot 24 of the tongue 23 and the anchor end 18. Accordingly, additional bonding methods for securing the strap 10 to the base are unnecessary. In addition, according to various embodiments, the tongue 23 allows the lower surface 14 of the engaging end 17 of the strap 10 to pass easily through the opening 26 in the strap 10, which may prevent the need for a two-handed assembly of the strap 10 relative to a base.

The intermediate portion 22 of the slit 19 shown in FIG. 2 has a generally arcuate shape. However, in another embodiment, such as shown in FIG. 4, the intermediate portion 42 of the slit 39 and the foot 44 of the tongue 43 form a generally triangular shaped opening (not shown) when the engaging end 37 of the strap 30 is pulled toward the anchor end 38. In yet another embodiment, such as shown in FIG. 5, the intermediate portion 62 of the slit 59 and the foot 64 of the tongue 63 form a generally rectangular shaped opening (not shown) when the engaging end 57 of the strap is pulled toward the anchor end 58.

In the embodiment shown in FIG. 6, the strap 70 includes an elongated body 73 that defines a first slit 79 and a second slit 89. The first slit 79 may be similar to the slits described above in relation to FIGS. 2-5 in that the ends 81a, 81b of the slit 79 are disposed toward the anchor end 78 relative to the intermediate portion 82 of the slit 79 along the longitudinal axis B of the elongated body 73. The second slit 89, however, includes two ends 91a, 91b that are disposed toward the engaging end 77 relative to the intermediate portion 92 of the slit 89 along the longitudinal axis B. According to one embodiment, having the second slit 89 prevents a user from attempting to assemble the strap 70 around one or more objects using the anchor end 78 of the strap 70.

According to various embodiments, the strap 10 may be formed of nylon, polyester, HDPE, vinyl, or other suitable material. In a particular embodiment, the strap 10 and the plurality of hooks are integrally formed. In addition, although the embodiments described above include hook fasteners along at least a portion of the lower surface thereof, in other embodiments, the lower surface of the strap may comprise loop material for engaging a field of hooks.

In an alternative embodiment (not shown), at least a portion of the lower surface of the strap may include a field of hooks, and at least a portion of the upper surface may include loop material. When the user wraps the engaging end of the strap around an item and pulls the engaging end through the slit, the upper surface of the engaging end can be engaged onto the lower surface of the strap above the slit. Alternatively, the lower surface of the engaging end may be wrapped around the item, pulled through the slit, and engaged onto the upper surface of the tongue. Similarly, in yet another embodiment, at least a portion of the upper surface of the strap may include a field of hooks and at least a portion of the lower surface may include loop material.

Assembly of Strap with Base

According to various embodiments, a hook and loop fastener assembly is provided for securing one or more objects adjacent a base with a fastening strap. As shown in the embodiment shown in FIGS. 7A-7B, the assembly includes a base 100 and the fastening strap 10 described above and shown in FIGS. 2 and 3. The base 100 includes an upper surface 112, and at least a portion of the upper surface 112 defines loop material for engaging a plurality of hooks on the lower surface 14 of the fastening strap 10. To secure said one or more objects 200, such as, for example, a catheter, adjacent the strap 10 and base 100, the one or more objects 200 are disposed adjacent the foot 24 of the tongue 23 of the strap 10. The engaging end 17 of the strap 10 is pulled upwardly from the base 100 and toward the anchor end 18, as shown in FIG. 7A, and the engaging end 17 is then threaded between the one or more objects 200 and the tongue 23 through the opening 26 defined by the foot 24 of the tongue 23 and the leg portions 25a, 25b, as shown in FIG. 7B. The engaging end 17 is then pulled away from the tongue 23 in the direction of the longitudinal axis A of the strap 10 to secure the strap 10 around the one or more objects 200, and at least a portion of the lower surface 14 of the elongated body 13 that has passed through the opening 26 is engaged onto the base 100, as shown in FIG. 7C.

In one embodiment, the base 100 includes an adhesive material (not shown) on its lower surface, which can be used to apply the base 100 to the skin of a patient, such as when a catheter is being held in position by the assembly. However, in various other embodiments, the base 100 may be adhered to another object, such as a wall or an appliance, when the assembly is used to hold cables or wires together, for example.

In addition, as noted above, in various other embodiments, the base 100 may include a plurality of hooks, and the lower surface of the strap 10 may include loop material.

In one embodiment, which is shown in FIGS. 8A and 8B, the base 300 defines a generally rectangular shaped hole 302, and the lower surface of the anchor end of a strap is engaged onto the upper surface of the base 300. In a particular embodiment, the tongue of the strap is positioned adjacent a first side of the hole 302. To secure one or more objects 400 adjacent the strap and base 300, the one or more objects 400 are positioned generally transverse to the longitudinal axis of the strap adjacent the anchor end, and the engaging end of the strap is wrapped over the one or more objects 400 and below the base 300. The engaging end is then thread through the hole 302 from the lower surface of the base 300 toward the upper surface of the base 300 and pulled through the hole 302 so that the strap is substantially taunt around the one or more objects 400. To prevent the strap from releasing the one or more objects 400, the lower surface of the portion of the strap that has been pulled through the hole 302 is engaged against the upper surface of the base 300 adjacent a second side of the hole 302 that is opposite the first side of the hole 302. Alternatively, the strap may be wrapped over the one or more objects 400, thread between the one or more objects 400 and the tongue, pulled through the opening of the strap, and engaged onto the upper surface of the base 300, as described in relation to FIGS. 7A-7C. In addition, although the hole 302 is described above as being generally rectangular, it may have any other shape capable of receiving the engaging end of the strap used therethrough.

CONCLUSION

Although this invention has been described in specific detail with reference to the disclosed embodiments, it will be understood that many variations and modifications may be effected within the spirit and scope of the invention as described in the appended claims.

The invention claimed is:

1. A hook and loop fastener assembly for securing one or more objects adjacent a base, said assembly comprising:
   a base comprising an upper surface, at least a portion of said upper surface defining one of a field of hooks or loop material; and
   a strap for securing one or more objects adjacent said base, said strap being separately formed from said base, said strap comprising:
      an upper surface;
      a lower surface opposite said upper surface, at least a portion of said lower surface comprising one of loop material or a field of hooks for engaging said hooks or said loop material, respectively, of said base;
      an anchor end;
      an engaging end; and
      an elongated body extending between said anchor end and said engaging end;
   wherein:
      said elongated body defines a slit, said slit having two ends and an intermediate portion between said ends of said slit, said ends of said slit being disposed toward said anchor end relative to said intermediate portion along a longitudinal axis of said elongated body;
      said elongated body comprises:
         a tongue disposed between said ends of said slit and said intermediate portion of said slit, at least a portion of said lower surface of said tongue comprising one of loop material or a field of hooks adapted for engaging said hooks or said loop material, respectively, of said base, and
         two leg portions disposed laterally adjacent each side of said slit and said tongue relative to said longitudinal axis, said leg portions having a combined width that is less than a width of a foot of said tongue, said foot of said tongue being disposed along a substantially transverse axis that extends through said ends of said slit, and
      said engaging end has a width that is less than said width of said foot of said tongue to allow said engaging end to pass through an opening defined by said foot of said tongue and said leg portions when said engaging end of said strap is wrapped around said one or more objects.

2. The hook and loop fastener assembly of claim 1 wherein to secure said one or more objects adjacent said strap, said one or more objects are disposed adjacent said foot of said tongue, said engaging end is pulled upwardly from said base and toward said anchor end and is threaded between said one or more objects and said tongue through said opening defined by said foot of said tongue and said leg portions, and at least a portion of said lower surface of said elongated body that has passed through said opening is engaged onto said base.

3. The hook and loop fastener assembly of claim 1 wherein said base comprises an adhesive material on said lower surface.

4. The hook and loop fastener assembly of claim 1 wherein a shear force between said strap and said foot of said tongue is substantially greater than a peeling force required to peel said engaging end and said leg portions upwardly from said base.

5. The hook and loop fastener assembly of claim 1 wherein said transverse axis that extends through said ends of said slit is substantially perpendicular to said longitudinal axis.

6. The hook and loop fastener assembly of claim 1 wherein said intermediate portion of said slit is generally arcuate shaped.

7. The hook and loop fastener assembly of claim 1 wherein said intermediate portion of said slit and said foot of said tongue form a generally triangular shaped opening when said engaging end of said strap is pulled toward said anchor end.

8. The hook and loop fastener assembly of claim 1 wherein said intermediate portion of said slit and said foot of said tongue form a generally rectangular shaped opening when said engaging end of said strap is pulled toward said anchor end.

9. The hook and loop fastener assembly of claim 1 wherein said slit is a first slit and said elongated body further defines a second slit, said second slit having two ends and an intermediate portion, wherein:

said two ends of said second slit are disposed toward said engaging end relative to said intermediate portion of said second slit along said longitudinal axis of said elongated body.

10. The hook and loop fastener assembly of claim 9 wherein said tongue is a first tongue and said leg portions are said first leg portions, and wherein said elongated body further defines a second tongue disposed between said intermediate portion of said second slit and said ends of said second slit and two second leg portions disposed laterally adjacent each side of said second slit and said second tongue relative to said longitudinal axis, said second leg portions having a combined width that is less than a width of a foot of said second tongue, said foot of said second tongue being disposed along a substantially transverse axis that extends through said ends of said second slit.

11. The hook and loop fastener assembly of claim 1 wherein said lower surface of said strap comprises a plurality of hooks that are integrally formed with said lower surface.

12. The hook and loop fastener assembly of claim 11 wherein said strap and said hooks integrally formed with said lower surface of said strap are formed of a nylon material.

13. The hook and loop fastener assembly of claim 1 wherein said elongated body comprises an engaging portion, said engaging portion comprising said engaging end and having a width that is less than said width of said foot of said tongue portion.

* * * * *